United States Patent
Measamer et al.

[11] Patent Number: 5,735,874
[45] Date of Patent: Apr. 7, 1998

[54] VARIABLE POSITION HANDLE LOCKING MECHANISM

[75] Inventors: John P. Measamer; Hector Chow, both of Cincinnati; Frederick J. Reber, II, Lebanon; Steven W. Hamblin, Loveland; James H. Chambers, Bowling Green, all of Ohio

[73] Assignee: Ethicon Endo-Surgery, Inc., Cincinnati, Ohio

[21] Appl. No.: 668,989

[22] Filed: Jun. 21, 1996

[51] Int. Cl.⁶ ................................ A61B 17/28
[52] U.S. Cl. .............. 606/208; 81/329; 81/331
[58] Field of Search ............... 606/208; 81/319, 81/320, 323, 329, 331, 339

[56] References Cited

U.S. PATENT DOCUMENTS

| | | | |
|---|---|---|---|
| 804,229 | 11/1905 | Hutchinson . | |
| 1,452,373 | 4/1923 | Gomez . | |
| 1,659,112 | 2/1928 | Littlejohn . | |
| 1,944,116 | 1/1934 | Stratman | 81/49 |
| 4,428,374 | 1/1984 | Auburn | 128/318 |
| 4,538,485 | 9/1985 | Saila | 81/320 X |
| 4,662,371 | 5/1987 | Whipple et al. | 128/312 |
| 4,712,545 | 12/1987 | Honkanen | 128/305 |
| 4,935,027 | 6/1990 | Yoon | 606/146 |
| 5,009,661 | 4/1991 | Michelson | 606/170 |
| 5,147,357 | 9/1992 | Rose et al. | 606/49 |
| 5,176,702 | 1/1993 | Bales et al. | 606/208 |
| 5,314,424 | 5/1994 | Nicholas | 606/41 |
| 5,476,479 | 12/1995 | Green et al. | 606/205 |
| 5,478,347 | 12/1995 | Aranyi | 606/170 |
| 5,483,952 | 1/1996 | Aranyi | 600/131 |
| 5,486,189 | 1/1996 | Mudry et al. | 606/171 |
| 5,496,347 | 3/1996 | Hashiguchi et al. | 606/205 |
| 5,613,977 | 3/1997 | Weber et al. | 606/208 |

FOREIGN PATENT DOCUMENTS

| | | | |
|---|---|---|---|
| 836545 | 4/1952 | Germany | 606/208 |
| 6-304177 | 11/1994 | Japan | 606/208 |
| WO 95/14435 | 6/1995 | WIPO . | |

*Primary Examiner*—Michael H. Thaler

[57] ABSTRACT

A surgical handheld instrument which is used in a minimally invasive surgical procedure such as a laparoscopic surgical procedure comprises a handle body and an elongated shaft connected to the handle body at a proximal end of the shaft. An end effector such as a pair of movable jaws are located at the distal end of the shaft. An actuation handle member is movably connected to the handle body and is operatively connected to the end effector for actuating movement of the end effector. Thus, upon movement of the handle actuation member, the end effector, such as movable jaw elements, can be opened or closed. The handle body also includes a locking tab, having a Z-shaped configuration wherein one end of the locking tab has a hole therethrough. An arcuate locking rod having a smooth, uniform surface is connected at one end to the handle actuation member and is insertable at its opposite end through the hole of the locking tab such that the arcuate locking rod is in movable contact with the locking tab. A release trigger is operatively connected to the locking tab for releasing contact of the arcuate locking rod and the locking tab. A biasing spring is included in the handle body for biasing the locking tab against the release trigger in a locked position.

22 Claims, 7 Drawing Sheets

VARIABLE POSITION HANDLE LOCKING MECHANISM

BACKGROUND OF THE INVENTION

The present invention relates, in general, to handheld surgical instruments and, in particular, to a new and useful locking mechanism for the handle of an endoscopic handheld instrument.

In minimally invasive surgery, elongated shaft instruments are used through access ports such as trocars to grasp, cut, dissect, and manipulate tissue. These instruments have a handle which is located external to the body for controlling the end effector of the instrument by the surgeon. Generally, these instruments have coaxial shafts which are used for sealing against the trocar and for transferring motion and force through the trocar to the end effector for performing a function such as cutting, grasping, or dissecting tissue. Typically, a rotation knob is associated with the coaxial shafts to allow for rotation of these shafts. Additionally, some handheld instruments are provided with attachments for monopolar and bipolar energy. Accordingly, these types of instruments normally have electrical insulation covering the coaxial shafts in order to protect the surgeon and patient.

The rigors of minimally invasive surgery dictate that the handheld instruments address certain functions such as proper ergonomics, control, and tactile feedback through the handle. These functions are imperative for the surgeon to properly perform the surgical procedure. Minimally invasive surgical instruments that provide for rough movement complicate the procedure and often frustrate the surgeon because the surgeon is further removed from the traditional touch and feel of surgery normally associated with open surgical procedures.

For some surgical procedures, a clamp feature on the handheld instrument is often required for the purpose of holding retraction or providing fixed position manipulation. A clamping feature is traditionally provided on surgical instruments used in open surgery and is deemed an important feature in minimally invasive surgical procedures. Generally, these instruments have scissor style handles with a toothed rack on one actuator handle arm, and a mating pawl on the other actuating handle arm. The latching takes place along the medial plane of the instrument as described in U.S. Pat. No. 1,659,112 (Littlejohn).

It is important to note that this type of clamping method is effective for traditional or open surgical instruments, but minimally invasive or laparoscopic instruments are typically provided with pistol grip handles making this type clamping action cumbersome and largely ineffective. An alternate method for clamping pistol grip handles of endoscopic handheld instruments is disclosed in U.S. Pat. No. 5,176,702 (Bales). In this design, a rack is mounted at the bottom of the movable portion of the handle, and a locking pawl is mounted at the bottom of the stationary portion of the handle. As the two handle halves are urged toward each other, the pawl and rack engage, locking the handle in that position. The rack is released by moving the pawl away from the rack using a camming mechanism. However, due to the undercut on the rack/pawl interface, pressure between the rack and pawl must first be relieved by urging the movable handle portion closer to the stationary portion, thereby effecting release. One major drawback to this type of handle locking feature, which is cause for concern among surgeons, is that, to effect release, additional pressure and load is placed on the tissue held within the jaws of the end effector of the instrument.

Another method used for effecting clamping in a handheld surgical instrument is described in U.S. Pat. No. 5,483,952 (Aranyi) and U.S. Pat. No. 5,476,479 (Green, et al.) wherein a rack is mounted directly on the actuation member which transfers motion and force from the handle to the end effector. A pawl is mounted on the stationary portion of the handle and is movably engaged to the rack. When the pawl is urged toward the rack, it will engage with the teeth of the rack, in increments, as the actuation rod is moved longitudinally during actuation. A major drawback to this design is that the pawl must be coupled to a release trigger with substantial mechanical advantage due to the high force required to disengage the pawl from the rack under a loaded condition. In addition, in order to gain usable resolution on the locking mechanism, and to maintain clamping pressure, either very small teeth must be used on the rack, or additional compliance must be built into the actuation assembly distal to the locking rack. Another drawback to this type of design is that the locking mechanism is restricted to locking the actuation system in discrete or pre-determined positions, usually five to ten different positions. This causes the surgeon to have to select a clamping force, which ultimately, may be too weak or too strong.

Another known handheld instrument feature is a locking design such as that disclosed in U.S. Pat. No. 804,229 (Hutchinson) and U.S. Pat. No. 5,314,424 (Nicholas). Both of these references describe a locking mechanism which is locked directly on the actuation rod of the instrument. However, this type of locking arrangement is limited in resolution requiring additional compliance to be built into the actuation assembly to be effective.

Until now, there is no known handle locking mechanism for a surgical handheld instrument which overcomes the drawbacks of the prior art devices mentioned above.

SUMMARY OF THE INVENTION

The present invention is a surgical handheld instrument which is used in a minimally invasive surgical procedure such as a laparoscopic surgical procedure. The present invention is a surgical handheld instrument which comprises a handle body and an elongated shaft connected to the handle body at a proximal end of the shaft. An end effector such as a pair of movable jaws are located at the distal end of the shaft. The end effector can be any type of surgical end effector such as forceps, scissors, graspers or the like.

The present invention also includes an actuation handle member which is movably connected to the handle body and is operatively connected to the end effector for actuating movement of the end effector. Thus, upon movement of the handle actuation member, the end effector, such as movable jaw elements, can be opened or closed.

Mounted within the handle body is a locking mechanism consisting of a locking tab, having a Z-shaped configuration wherein one end of the locking tab has a hole therethrough, a biasing spring for maintaining the locking tab in a locking orientation, and a release trigger acting against said locking tab for effecting release. An arcuate locking rod having a smooth, uniform surface is connected at one end to the handle actuation member and is insertable at its opposite end through the hole of the locking tab such that the arcuate locking rod is in movable contact with the locking tab.

The locking rod is positioned on the actuation member at a point radially distanced from the pivot point of the actuation member.

Mounting the locking rod in this position provides for increased resolution of movement of the locking rod with respect to the movement of the actuation rod, offering improved resolution and control of the locking position.

Further, mounting the locking rod in this position takes advantage of the natural compliance within the total actuation system, further improving resolution of the locking position.

Further, mounting the locking rod in this position, improves the mechanical advantage of the force generated by the locking tab holding to the locking rod, improving the effectiveness of the locking mechanism, and reducing the force necessary to effect release.

A release trigger is operatively connected to the locking tab for releasing contact of the arcuate locking rod and the locking tab. A biasing spring is included in the handle body for biasing the locking tab against the release trigger in a locked position.

The locking tab is mounted within the handle body such that it freely pivots. Additionally, the hole in the locking tab is greater than the diameter of the arcuate locking rod for providing an unidirectional, frictional locking action on the arcuate locking rod when disposed at an angle relative to a line perpendicular to the tangent line at the contact point with the locking rod. The Z-shaped configuration of the locking tab allows for a compact layout within the handle body and provides an effective pivot point. Since the locking rod has a smooth surface, and not a grooved surface or toothed surface normally associated with the rack and pawl designs in the prior art, it allows for clamping in any position along the locking rod, which, in turn, provides the surgeon total control over clamping force and pressure over any thickness of tissue. The mechanism's smooth design also avoids accumulating debris or holding contamination thereon.

The release trigger is located external to the handle body and is disposed to move in a direction parallel to the longitudinal axis of the handheld instrument. Since the locking tab is spring biased to a locked position, release of the locking tab is accomplished by depressing the trigger which, in turn, presses against the bottom portion of the locking tab. The Z-shape of the locking tab permits pivoting of the locking tab removing the frictional locking force which allows the arcuate locking rod to move through the hole in the locking tab effecting release.

The release trigger is also provided with a notch which engages a protrusion on the handle body which serves as a trigger locking means. This is activated or released by moving the trigger in an upward or downward direction roughly perpendicular to the longitudinally axis of the instrument at the fully depressed position of the release trigger stroke. When activated, the release trigger is retained so as to hold the locking tab in the unlocked position providing for unrestricted bi-directional motion of the actuation system.

The present invention also includes finger loops on both the handle body and the handle actuation member. A finger rest portion extends below the finger loop on the handle body which permits the surgeon's small finger to engage the finger rest portion for improved control of the instrument and enhanced ergonomic effect.

It is an object of the present invention to provide a handle locking mechanism for a surgical handheld instrument which allows for total variability in the locking position of the end effector.

It is another object of the present invention to provide a locking mechanism which prevents malfunction due to debris accumulation or contamination.

It is another object of the present invention to provide a handle locking mechanism which allows for release of the end effector independent of the actuation handle such that when a release trigger is depressed, the lock releases without having to move the actuation handle.

It is another object of the present invention to provide a handle locking mechanism which is smooth in function and quiet in operation.

It is another object of the present invention to provide a handle locking mechanism which permits the end effector of the instrument to be easily disengaged at the user's discretion.

It is another object of the present invention to provide a handle locking mechanism which permits a user controllable holding force on the end effector by using the natural compliance of the actuation system thereby allowing for greater resolution of locking.

It is another object of the present invention to provide a handle locking mechanism which is capable of being locked in any position along the actuation stroke as is required by the clinical application or surgeon preference.

It is another object of the present invention to provide a handle locking mechanism for a surgical handheld instrument which is simple to manufacture and easy to assemble.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
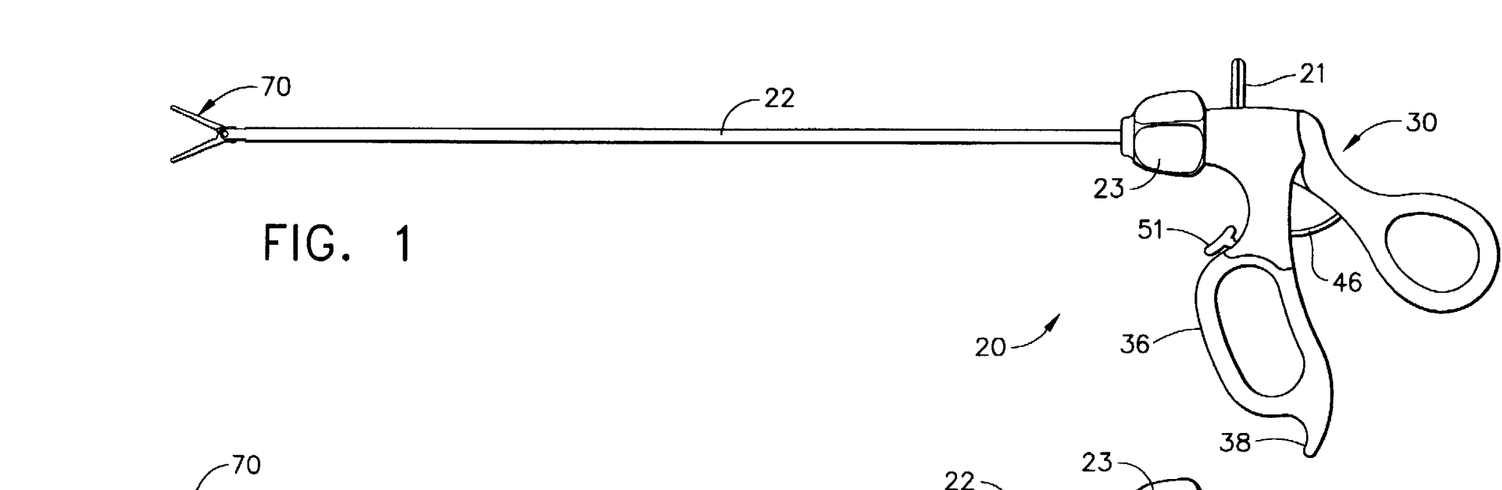
FIG. 1 is a side elevational view of a preferred embodiment of a laparoscopic instrument with variable position handle locking mechanism.
Figures 2, 3:
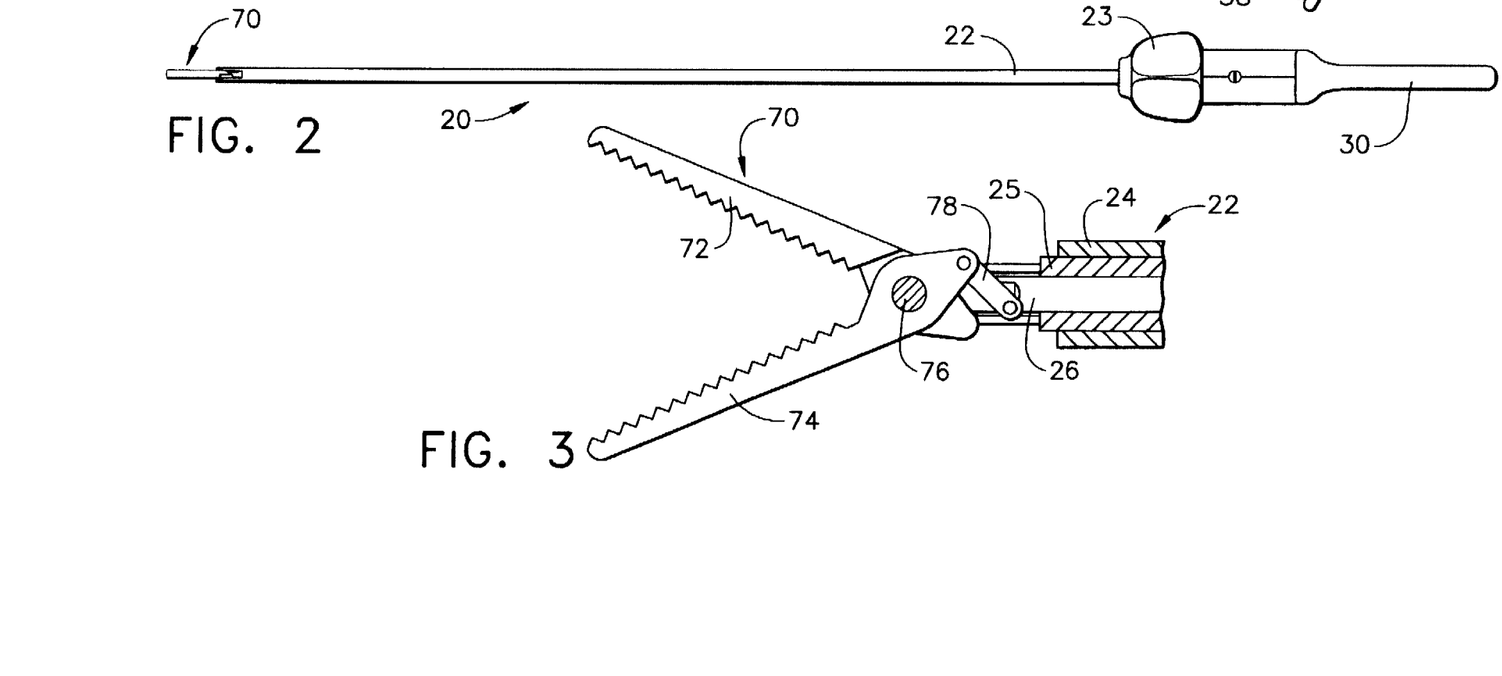
FIG. 2 is a plan view of the laparoscopic instrument of FIG. 1.
FIG. 3 is a fragmentary side elevational view partially in section of the distal end of the laparoscopic instrument of FIG. 1.

The present invention, as best shown in FIGS. 1 and 2, is a surgical handheld instrument, generally designated 20, for use in minimally invasive surgical procedures such as laparoscopic procedures. The instrument 20 comprises a handle 30, an elongated shaft 22 connected to the handle 30 and an end effector assembly 70 such as a pair of movable jaw members 72 and 74 (FIG. 3) operatively connected to the shaft 22 for grasping tissue therebetween. A rotation knob 23 is connected to the shaft 22 and the handle 30 for providing rotation of the shaft 22 and end effector assembly 70.

As illustrated in FIG. 3, the shaft 22 is coated with an insulating material 24, which protects the surgeon and patient during the use of electrocautery. The shaft 22 is coaxial and comprises insulation layer 24 superimposed over an outer shaft 25 with an actuation rod 26 movably positioned therein. A jaw linkage assembly 78 is connected to the actuation rod 26 and the end effector assembly 70 such that jaw members 72 and 74 can be opened and closed by movement around pivot pin 76 as actuation rod 26 is slidably moved within the shaft 22.

Figure 4:
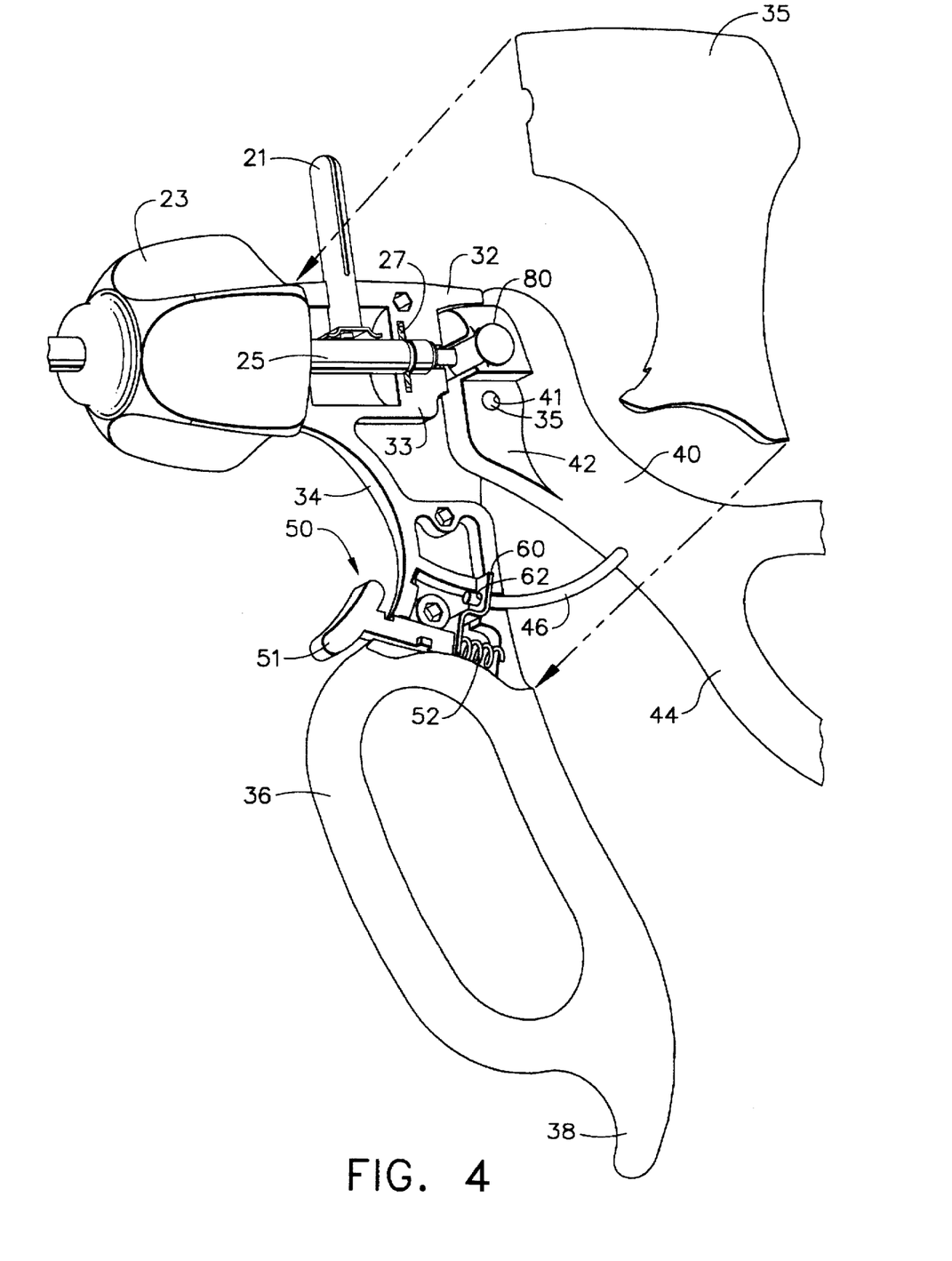
FIG. 4 is an isometric view of the proximal end of the laparoscopic instrument of FIG. 1 with a left side handle cover in exploded disposition to reveal internal parts thereof.

As shown in FIG. 4, the handle 30 comprises a handle body 32 and a handle actuation section 40. The outer shaft 25 and rotation knob 23 are connected to the handle body 32. The handle body 32 comprises a barrel 33 in the upper section of the body 32. A handle neck 34 extends downwardly therefrom and a lower finger loop 36 is connected thereto. The body 32 is split along the media/plane parallel to the longitudinal axis of the instrument 20, forming an upper cover 35a which covers the barrel 33 of the body 32 and the neck 34. Finger loop 36 has a small finger rest 38 extending from a bottom portion of the loop 36 for contacting the small finger or pinkie finger of the surgeon. The finger rest portion 38 provides improved control as well as enhances ergonomic aspects.

Figure 5:
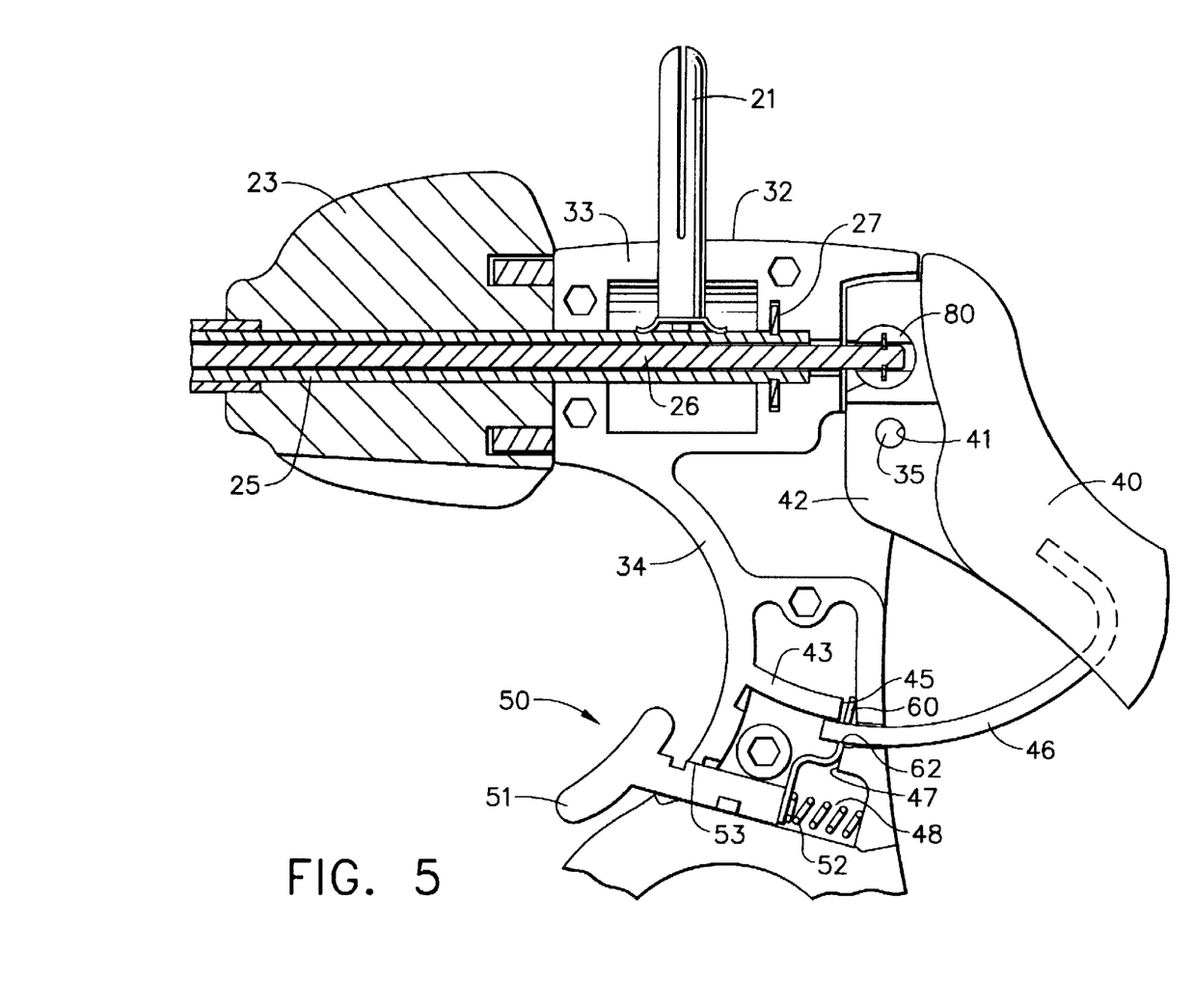
FIG. 5 is a side elevation view in centerline section with the left side handle cover removed.

As illustrated in FIGS. 4 and 5, the barrel 33 contains an attachment ring 27 which connects the outer shaft 25 to the body 32. A cautery pin 21 for electrocautery is in contact with the outer shaft 25 and extends through the body 32. The neck 34 contains a handle locking assembly 50 consisting of a locking tab 60, a release trigger 51, and a locking tab biasing spring 52. Greater detail of the locking assembly 50 is provided below.

The handle actuation section 40 is provided with an actuation finger loop 44. The actuation section 40 is pivotably connected to the handle body 32 at the barrel 33 and has a pivot hole 41 in a hub 42 which mates with a pivot post 35 on the handle body 32. An attachment assembly 80 pivotably connects the actuation rod 26 to the handle actuation section 40 such that when the actuation section 40 is moved about pivot post 35, the actuation rod translates in response thereto. When the actuation section 40 is moved away from the handle body 32, the actuation rod 26 is advanced longitudinally toward the end effector assembly 70 thereby opening the jaw members 72 and 74. When the actuation section 40 is moved towards the handle body 32, the actuation rod is retracted thereby closing the jaw members 72 and 74.

An arcuate locking rod 46 is fixed to the actuation section 40 at one end and is movably connected to the neck 34 of the body 32 at its opposite end. The locking rod 46 is arcuate in shape and is coplanar with the medial plane of actuation section 40. The locking rod 46 is attached to the actuation section 40 at a point radially distanced from the pivot hole 41 and hub 42 of the actuation section 40.

Figures 6, 7, 8:
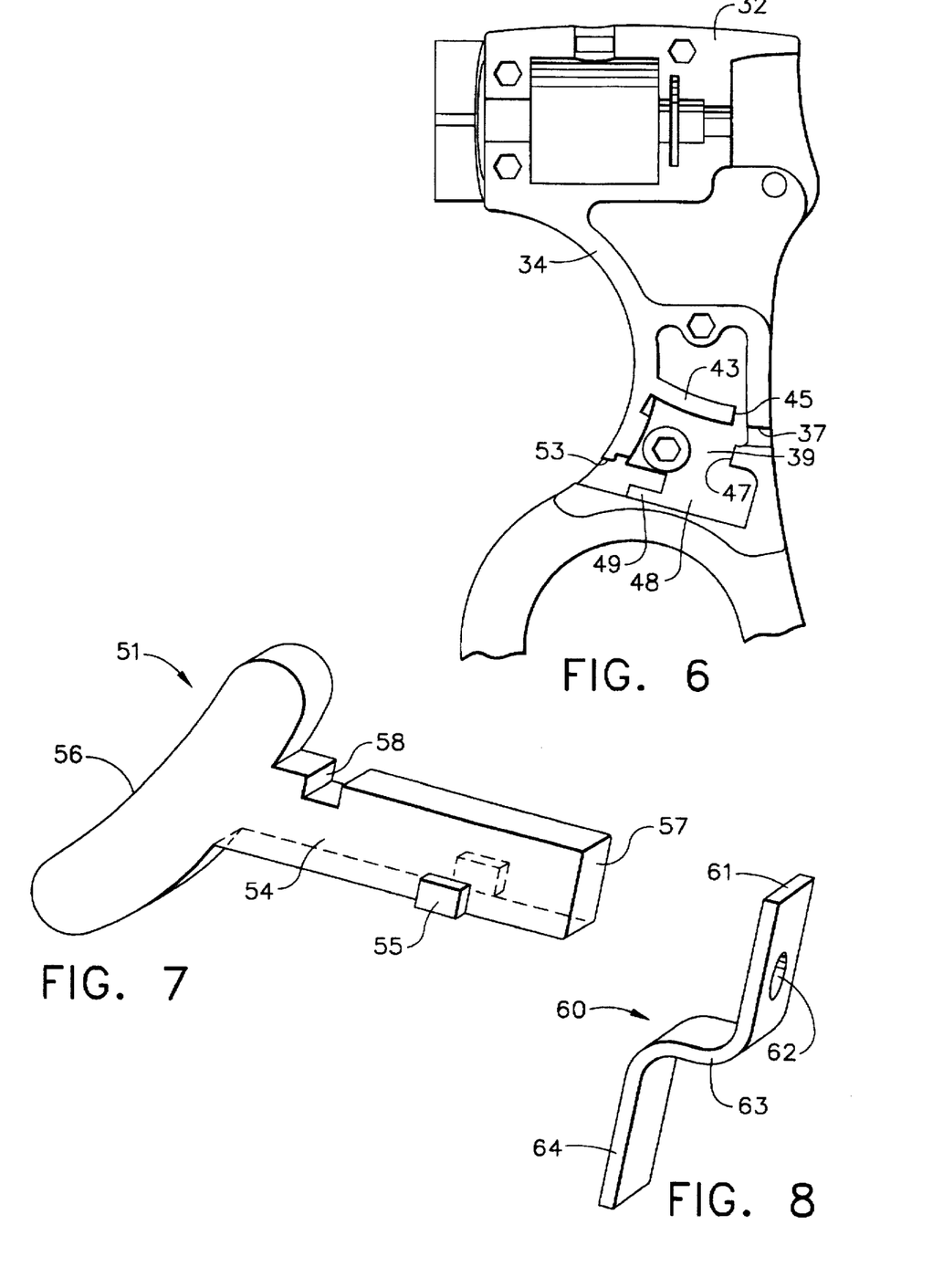
FIG. 6 is a left side upright view of the right side member of the handle shown without internal parts for clarity with the lower portion of the handle having been truncated.
FIG. 7 is an isometric view of a release button incorporated into the laparoscopic instrument of FIG. 1.
FIG. 8 is an isometric view of a spring lock incorporated into the laparoscopic instrument of FIG. 1.

FIG. 6 shows the inside of the neck 34 of the handle body 32 wherein the neck 34 has an aperture 37 therethrough and a cavity 39 therein for allowing the locking rod 46 to enter the neck cavity 39 through the aperture 37. The neck 34 also has an arcuate shoulder 43 which abuts and guides the locking rod 46 as the actuation section 40 and locking rod 46 are advanced toward the handle body 32. The shoulder 43 has a stop 45 for restricting the motion of the locking end 61 of the locking tab 60 (FIG. 8) to a position perpendicular to the tangent line at the point of contact between the locking tab and the locking rod. The neck 34 also has a pivot shoulder 47 about which the locking tab 60 (FIG. 8) rotates. A pocket 48 is also located in the neck 34 for holding a locking tab biasing spring 52 (FIG. 5). A guide slot 49 is used to guide the locking release trigger 51 (FIG. 7) and a locking shoulder 53 is used to hold the locking release trigger 51 in a release position.

FIG. 8 illustrates the locking tab 60 which is a flat strip bent into a Z-shape. The locking end 61 of the locking tab 60 has a hole 62 which is sized to allow the locking rod 46 to pass freely through the hole when the tab is perpendicular to the tangent fine of the locking rod 46, but restricts motion in one direction when the locking tab is at an angle with respect to the line perpendicular to the tangent fine of the locking rod. Below the hole 62 is a first bend 63 of the Z-shaped tab 60 which forms a pivot point for the tab 60 as it contacts the pivot shoulder 47 of the neck 34. The lower portion 64 of the locking tab 60, in conjunction with the pocket 48 of neck 34, contains the locking tab biasing spring 52 therein and the lower portion 64 engages the spring 52.

Figure 9:
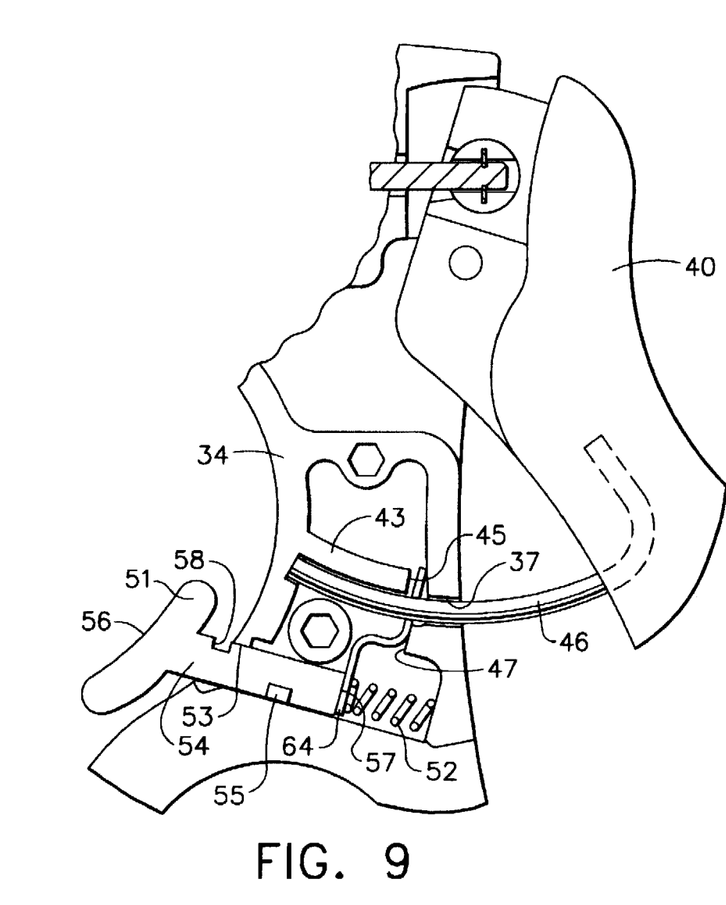
FIG. 9 is a left side upright view of the handle portion of the laparoscopic instrument of FIG. 1 with the left side cover removed to expose internal parts and their relationship with the instrument in the fully clamped and locked position.
Figure 10:
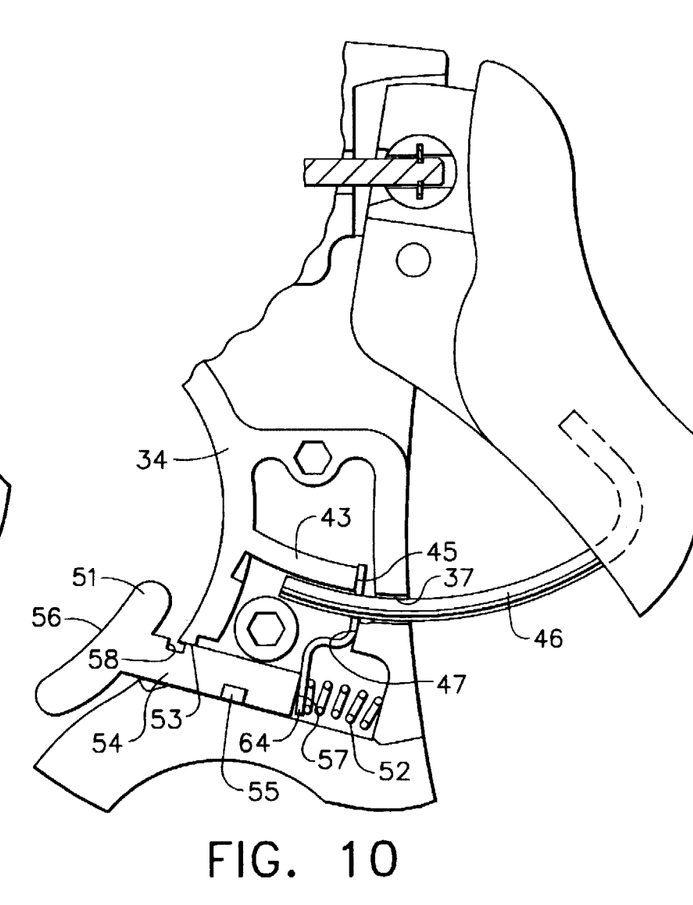
FIG. 10 is a left side upright view of the handle portion of the laparoscopic instrument of FIG. 1 with the left side cover removed to expose internal parts and their relationship with the instrument in a half open and unlocked position as the instrument is in the process of opening.
Figure 11:
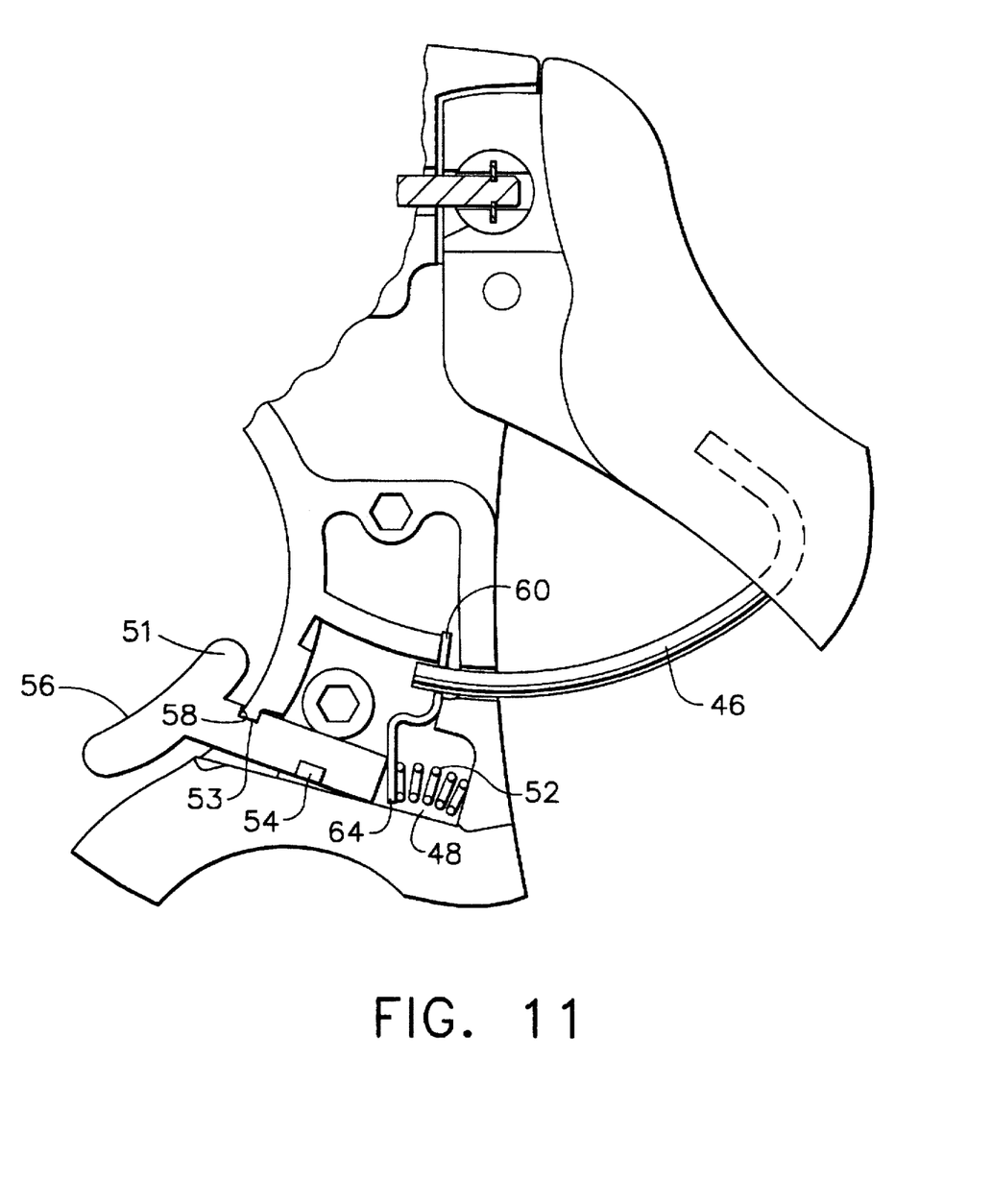
FIG. 11 is a left side upright view of the handle portion of the laparoscopic instrument of FIG. 1 with the left side cover removed to expose internal parts and their relationship with the instrument in an unlocked position permitting free manipulation of the handle and distal end without the aid of the locking mechanism.

FIG. 7 shows the release trigger 51 having a slide member 54 and two guide shoulders 55 on both sides of member 54. Guide shoulders 55 engage the guide slot 49 in the neck cavity 48 (FIG. 6). A pad 56 is located at the distal end of the release trigger 51 and protrudes from the neck 34 of the handle body 32 to receive the user's finger for actuation of the release trigger 51. A proximal end 57 of the release trigger 51 butts against the lower portion 64 of the locking tab 60 and opposes the biasing spring 52. Accordingly, as shown in FIGS. 9 and 10, the lower end 64 of the locking tab 60 is located between and contacts the proximal end 57 of the release trigger 51 and the biasing spring 52. A locking notch 58 is located on the upper portion of the trigger slide member 54 of the release trigger 51 and is sized and positioned such that the notch 58 engages the locking shoulder 53 on the neck 34 of the handle body 32 after the slide member 54 has been advanced into cavity 39 upon the depression of release trigger 51 and a slight upward motion is applied to release trigger 51 as illustrated in FIG. 11.

When assembled, the locking tab 60 is held in place between the proximal end 57 of the release trigger 51, pivot shoulder 47, and the stopping shoulder 45 of the locking rod guide 43. The locking rod 46 passes through the aperture 37 in the neck 34 of the body 32, and through the hole 62 in the locking tab 60. The locking tab 60 is predisposed at an angle with respect to a line perpendicular to the tangent line of the arc of the locking rod 46 which causes the tab 60 to frictionally lock on the locking rod 46 so as to oppose the retracting of the locking rod 46 from the body 32 of the instrument 20. The locking rod shoulder 43 serves as a buttressing surface for the locking rod 46 and assists in holding the locking rod 46 in position.

When in use, the locking assembly 50 of the present invention is actuated by the surgeon when it is desired to grasp and/or clamp tissue. The surgeon urges the actuation section 40 toward the neck 34 of the handle body 32 such that friction of the locking rod 46 against the through hole 62 in locking tab 60 causes a slight motion in the locking tab 60, urging it into a position perpendicular with respect to the tangent line of the arc of the locking rod 46 as best shown in FIGS. 9-11. As the tab 60 approaches this perpendicular orientation, the locking rod 46 freely moves through the hole 62 in the locking tab 60 allowing the handle actuation section 40 to move toward the handle body 32 which in turn causes the end effector assembly 70 to close upon the desired tissue. By continuing to urge the actuation section 40 toward the handle body 32, the tissue is clamped with the jaw members 72 and 74 of the end effector assembly 70. Through this compression, forces begin building up within the instrument actuation system, e.g., the end effector assembly 70, the linkage assembly 78, the actuation rod 26, the attachment assembly 80, the actuation section 40, and the trigger locking mechanism 50 resulting in strain in the actuation system. This swain allows the locking rod 46 to move an additional distance through the locking tab 60, further increasing the forces within the actuation system, which increases the clamping pressure on the tissue.

When pressure is released from the handle actuation section 40, the residual forces built up within the actuation system urge the actuation section 40 to its open position. As the locking rod 46 moves outwardly from the locking tab 60, the tab 60, assisted by bias spring 52, rotates about its pivot point 63 and is shifted to a position at an angle with respect to the line perpendicular to the tangent line of the arcuate locking rod 46. This causes frictional binding between the tab 60 and locking rod 46 thereby preventing further outward motion of the locking rod 46. Only a slight outward motion is permitted by the locking assembly 50 which is easily accommodated by the residual strain in the actuation system. The binding remains in effect until the release trigger 51 is depressed which causes the locking tab 60 to shift to a perpendicular orientation with respect to the tangent line to the arc of the locking rod 46 thereby relieving the binding against the locking rod 46 and effecting release.

If, when the trigger 51 is fully depressed, an upward motion is applied to the finger pad 56, the locking notch 58 engages the locking shoulder 53 which holds the locking tab 60 in an unlocked position thereby allowing for free bi-directional movement of the handle actuation section 40, i.e., toward and away from the handle body 32 as shown in FIG. 11. If a downward pressure is exerted on the pad 56, the release trigger 51 moves downward, disengaging the notch 58 from the shoulder 53 thereby allowing the release trigger 51 and locking tab 60 to return to the locked position, and consequently allowing only inward motion of the handle actuation section 40.

Figure 12:
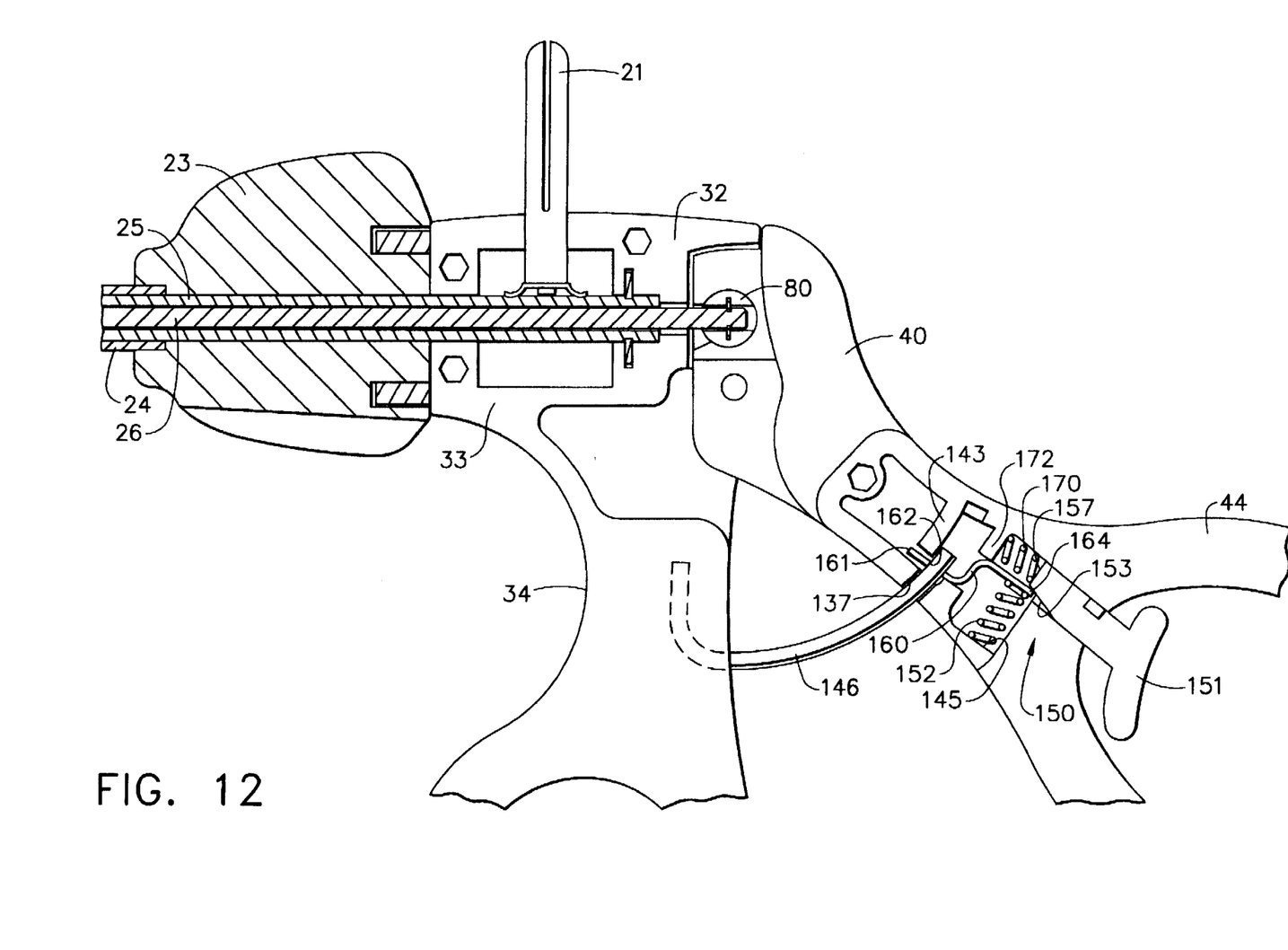
FIG. 12 is a side elevation view in centerline section of an alternative embodiment of a laparoscopic instrument with variable position handle locking mechanism with the right side handle cover removed.

An alternative embodiment of the present invention is shown in FIG. 12, wherein the same reference numerals used in FIGS. 1-11 are used to illustrate the same or like parts in the alternative embodiment. Elements that are common to both the alternative embodiment and the embodiment in FIGS. 1-11 are not shown in FIG. 12. In the alternative embodiment according to the present invention, as best illustrated in FIG. 12, the handle actuation section 40 has a release trigger 151 which is slidably disposed within the actuation section 40 at the actuation finger loop 44. The proximal end of the release trigger 151 is located within the actuation finger loop 44 while the distal end 157 of the release trigger 151 is located within the actuation section 40 and contacts a biasing spring 170. In turn, the biasing spring 170 contacts a wall 172 such that when the release trigger 151 is depressed, the distal end 157 of the trigger 151 compresses the spring 170 between the distal end 157 and the wall 172. The release trigger 151 also has an inclined surface 153 adjacent the distal end 157 of the trigger 151. The inclined surface 153 of the release trigger 151 contacts an end portion 164 of a locking tab 160. A locking tab biasing spring 152 is located between the lower end 164 of the locking tab 160 and an outer wall 145 of the actuation section 40.

The locking tab 160 is Z-shaped and has an upper end or locking end 161 opposite the lower end 164. The locking tab 160 has an aperture 162 in the locking end 161 for passing a locking rod 146 therethrough. The locking rod 146 is fixed at one end to the neck 34 of the handle body 32 and is slidably movable through a hole 137 in the actuation section 40. Additionally, an abutment surface 143 is located adjacent the locking rod 146 in the actuation section 40 for guiding the locking rod 146.

This alternative embodiment locks the actuation system in the same manner as described in the previous paragraphs. To release locking, the surgeon depresses the release trigger 151 with the thumb, which compresses spring 170 and causes movement of the locking tab 160 as the inclined surface 153 of the release trigger 151 is advanced past the lower end 164 of the locking tab 160 compressing the locking tab spring 152 and pivoting locking tab 160 to a perpendicular orientation with respect to the tangent line of the arc of the locking rod 146. This permits the locking rod 146 to freely move through aperture 137 and hole 162 in the locking tab 160. The locking mechanism 150 will return to a locked position once force is released from the release trigger 151 by the surgeon which will cause the locking tab 160 to shift its orientation such that it frictionally engages the locking rod 146 at the hole 162 in the locking end 161 of the locking tab 160.

Although this invention has been described in connection with its most preferred embodiments, it will become readily apparent to those reviewing this detailed specification that numerous additional embodiments fall well within the scope and spirit of the claimed invention as set forth in the claims which appear below.

What is claimed is:

1. A surgical instrument for grasping and clamping tissue comprising:

a handle body having a locking shoulder;

an elongated shaft having a proximal end and a distal end and connected to said handle body at said proximal end;

an end effector having at least one movable member located at said distal end of said shaft;

an actuation member movably connected to said handle body and operatively connected to said end effector for actuating movement of said at least one movable member;

a locking tab on said handle body and having a hole therethrough, said locking tab being movable between a locked position and an unlocked position;

a locking rod having a proximal end and a distal end, said locking rod being fixed to said actuation member at said proximal end, and wherein at least said distal end of said locking rod is movably engaged with said locking tab through said hole; and a release trigger slidable linearly in said handle body, said release trigger having a notch therein and operatively connected to said locking tab for releasing engagement of said locking rod and said locking tab from said locked position to said unlocked position, said notch being engageable with said locking shoulder of said body such that said locking tab is moved to said unlocked position, and wherein said actuation member has free bi-directional movement.

2. The surgical instrument according to claim 1, wherein the locking rod is arcuate in shape.

3. The surgical instrument according to claim 2, including a biasing spring on said handle body for biasing said locking tab against said release trigger.

4. The surgical instrument according to claim 3, wherein said handle body includes a finger loop.

5. The surgical instrument according to claim 4, wherein said handle body includes a finger rest portion extending below said finger loop.

6. The surgical instrument according to claim 5, wherein said actuating member includes a finger loop.

7. The surgical instrument according to claim 3, wherein said locking tab has a Z-shape.

8. The surgical instrument according to claim 7 wherein said locking tab has a top section with said hole therethrough and a bottom section which contacts said biasing spring and said release trigger.

9. The surgical instrument according to claim 3, wherein said release trigger includes a locking section for releasably engaging said handle body.

10. The surgical instrument according to claim 9, wherein said locking tab is biased in a locked position restricting movement of said locking rod.

11. The surgical instrument according to claim 1, including a rotation member connected to said shaft for rotating said shaft and said end effector.

12. A surgical instrument for grasping and clamping in tissue comprising:

a handle body;

an elongated shaft having a proximal end and a distal end and connected to said handle body at said proximal end;

an end effector having at least one movable member located at said distal end of said shaft;

an actuation member movably connected to said handle body and operatively connected to said end effector for actuating movement of said at least one movable member;

a locking tab on said actuation member and having a hole therethrough, said locking tab being movable between a locked position and an unlocked position;

a locking rod having a first end and a second end, said locking rod being fixed to said handle body at said first end, and wherein at least said second end of said locking rod is movably engaged with said locking tab through said hole; and a release trigger having an inclined surface operatively connected to said locking tab for releasing engagement of said locking rod and laid locking tab from said locked position to said unlocked position, said locking tab being movable on said inclined surface such that said locking tab is moved to said unlocked position, and wherein said actuation member has free bi-directional movement.

13. The surgical instrument according to claim 12, wherein the locking rod is arcuate in shape.

14. The surgical instrument according to claim 13, including a biasing spring on said handle body for biasing said locking tab against said release trigger.

15. The surgical instrument according to claim 14, wherein said handle body includes a finger loop.

16. The surgical instrument according to claim 15, wherein said handle body includes a finger rest portion extending below said finger loop.

17. The surgical instrument according to claim 16, wherein said actuating member includes a finger loop.

18. The surgical instrument according to claim 14, wherein said locking tab has a Z-shape.

19. The surgical instrument according to claim 18, wherein said locking tab has a top section with hole therethrough and a bottom section which contacts said biasing spring and said release trigger.

20. The surgical instrument according to claim 14, wherein said release trigger includes a locking section for releasably engaging said handle body.

21. The surgical instrument according to claim 20, wherein said locking tab is biased in a locked position restricting movement of said locking rod.

22. The surgical instrument according to claim 12, including a rotation member connected to said shaft for rotating said shaft and said end effector.

* * * * *

UNITED STATES PATENT AND TRADEMARK OFFICE
CERTIFICATE OF CORRECTION

PATENT NO. : 5,735,874
DATED      : April 7, 1998
INVENTOR(S): John P. Measamer et al.

It is certified that error appears in the above-identified patent and that said Letters Patent is hereby corrected as shown below:

Col. 9, Line 37, Claim 12: please delete -- in -- after "clamping".

Col. 10, Line 32, Claim 19: please add -- said -- after "with".

Signed and Sealed this

Thirtieth Day of May, 2000

Attest:

Q. TODD DICKINSON

Attesting Officer

Director of Patents and Trademarks